United States Patent [19]
Leight

[11] 3,943,925
[45] Mar. 16, 1976

[54] EAR PROTECTOR ASSEMBLY

[76] Inventor: Howard S. Leight, 16027 Northfield St., Pacific Palisades, Calif. 90272

[22] Filed: Sept. 12, 1974

[21] Appl. No.: 505,356

Related U.S. Application Data

[63] Continuation-in-part of Ser. No. 346,746, April 2, 1973, Pat. No. 3,856,007.

[52] U.S. Cl. .................................. 128/152; 2/3 R
[51] Int. Cl.² .......................................... A61F 11/00
[58] Field of Search ........ 128/152, 151; 2/185, 3 R, 2/3 C, 209; 179/182 R, 182 A, 107 S; 181/129, 130, 135

[56] References Cited
UNITED STATES PATENTS

| | | | |
|---|---|---|---|
| 1,167,368 | 1/1916 | Adams-Randall .............. | 128/152 X |
| 3,160,717 | 12/1964 | Beguin ............................. | 128/152 |
| 3,297,832 | 1/1967 | Brown ............................. | 181/130 X |
| 3,431,370 | 3/1969 | Crosby ........................... | 181/130 X |

Primary Examiner—Robert W. Michell
Assistant Examiner—Henry J. Recla
Attorney, Agent, or Firm—Lindenberg, Freilich, Wasserman, Rosen & Fernandez

[57] ABSTRACT

An ear protector assembly which can be easily put on and removed, including a mount which is readily attached to the temple bar of an eyeglass frame, an arm having an inner end pivotably connected to the mount, and an earplug fixed to an outer end of the arm. The mount has fasteners that enable a workman to clamp the mount at a location along the temple bar wherein the earplugs properly enter his ears, and thereafter every time he puts on his eyeglasses and pivots the arms inwardly the earplugs will properly enter his ears. The earplug assemblies are primarily useful for mounting on safety glasses, so that a workman has to put on only one apparatus to simultaneously protect his eyes and ears.

10 Claims, 7 Drawing Figures

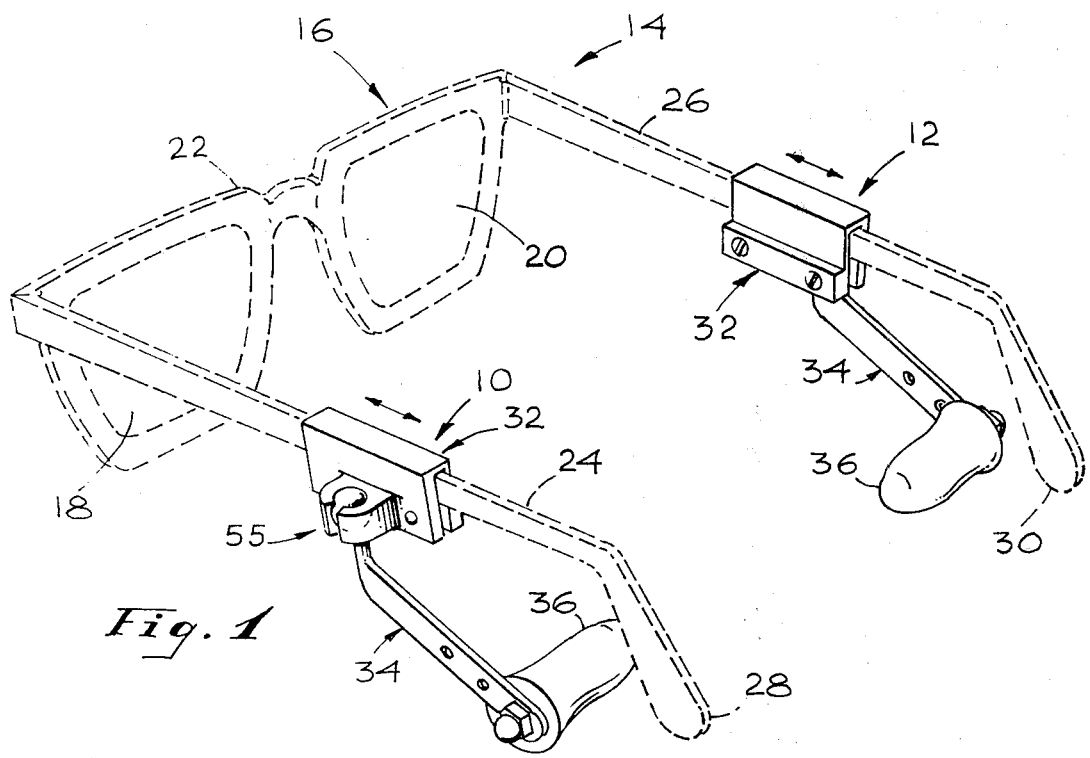
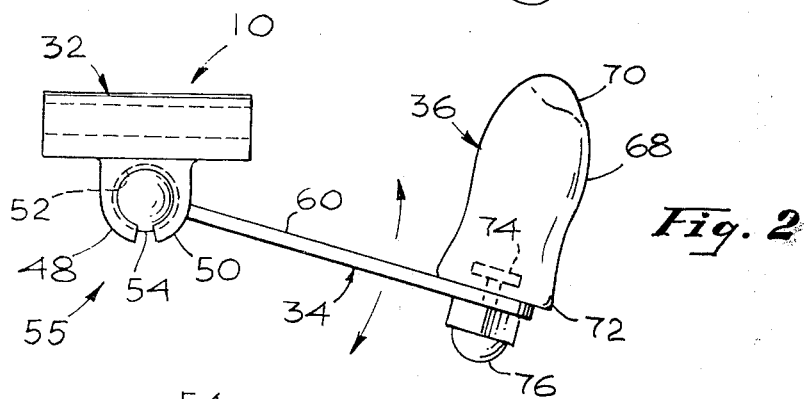
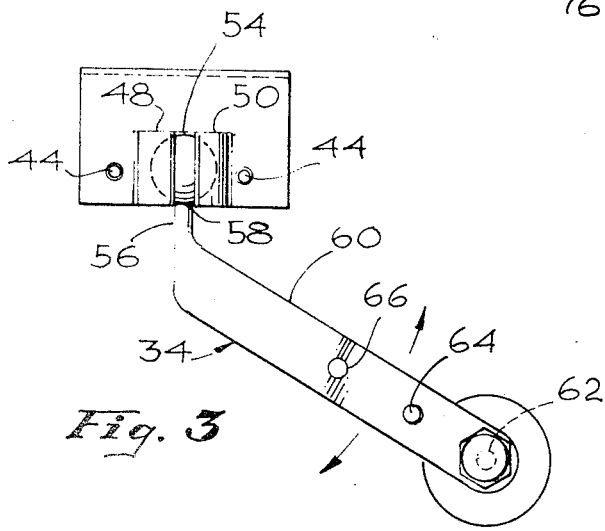
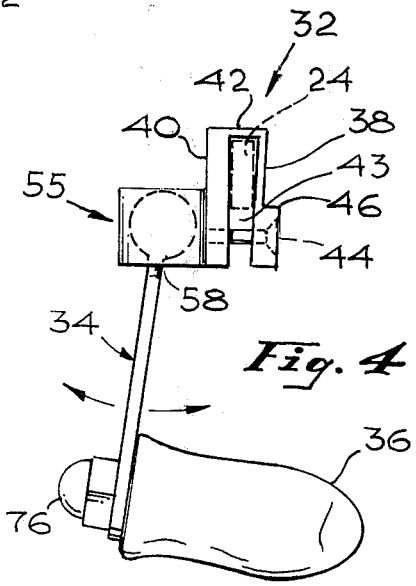

EAR PROTECTOR ASSEMBLY

CROSS-REFERENCE TO RELATED APPLICATION

This application is a continuation-in-part of patent application Ser. No. 346,746 filed Apr. 2, 1973 now U.S. Pat. No. 3,856,007.

BACKGROUND OF THE INVENTION

Ear protectors for blocking out loud noises are often worn by workmen who also must wear eyeglasses to protect their eyes and/or to correct for faulty vision. Such ear protectors, which normally include a band that fits over the head to support a pair of earplugs, are often considered inconvenient and annoying to workmen. This is because the ear protector constitutes another bulky item which has to be put on and taken off, and also because the bands are often annoying to adjust and often slip from the proper position.

SUMMARY OF THE INVENTION

In accordance with one embodiment of the present invention, an ear protector assembly is provided which can be mounted on eyeglasses, so that the eyeglass frame holds the earplugs in place on the workmen or other wearer and eliminates the need to handle and store a separate ear protector device. Furthermore, the assembly permits rapid and accurate insertion of the earplug into the ear whenever the eyeglass frame is worn. The ear protector assembly includes a mount that can be attached to a temple bar of an eyeglass frame, an arm pivotably connected at one end to the mount, and an earplug mounted at a second end of the arm. The assemblies are utilized in pairs, one attached to each temple bar of the eyeglass frame. A workman handles his eyeglasses and the ear protector assemblies thereon as a single unit, first placing the ear loops of the temple bars over his ears and then pivoting the arms so the earplugs enter his ears. The mount of each assembly is slideable along the temple bar and can be permanently clamped in a desired position therealong, so that the workman does not have to make any adjustment each time he puts on the eyeglasses other than to pivot the arms into position. The mount has a pair of walls that form a part-spherical socket, and the arm has a ball which is held in the socket and which is large enough to resiliently spread the socket walls apart so that there is high friction to retain the arm in any position to which it is pivoted. The fact that only pivotal movement is involved in moving the earplugs into position each time the ear protector is used, means that smooth operation can be attained in a low cost device.

In another ear protector apparatus, the mount is a two-piece assembly, with a first member left substantially permanently on the temple bar of an eyeglass frame, and with a second member which can be easily slipped onto the first member and taken off again. The second member pivotally supports the arm which holds the earplug. After a day of work, a workman can slip off the second member so that his eyeglass has a typical eyeglass appearance and is appropriate to wear at home. The apparatus also includes a torsion spring which urges the arm to pivot toward the head to firmly hold the earplug against the ear, but the torsion spring does not interfere with up and down pivoting of the arm which is necessary to position the earplug at the ear canal.

The novel features that are considered characteristic of the invention are set forth with particularity in the appended claims. The invention will be best understood from the following description when read in conjunction with the accompanying drawings.

BRIEF DESCRIPTION OF THE DRAWINGS

FIG. 1 is a perspective view of ear protector assemblies constructed in accordance with the invention, shown mounted on an eyeglass;

FIG. 2 is a plan view of an ear protector assembly of FIG. 1;

FIG. 3 is a side elevation view of the ear protector assembly of FIG. 2;

FIG. 4 is a rear elevation view of the ear protector assembly of FIG. 2;

DESCRIPTION OF THE PREFERRED EMBODIMENTS

Figure 5:
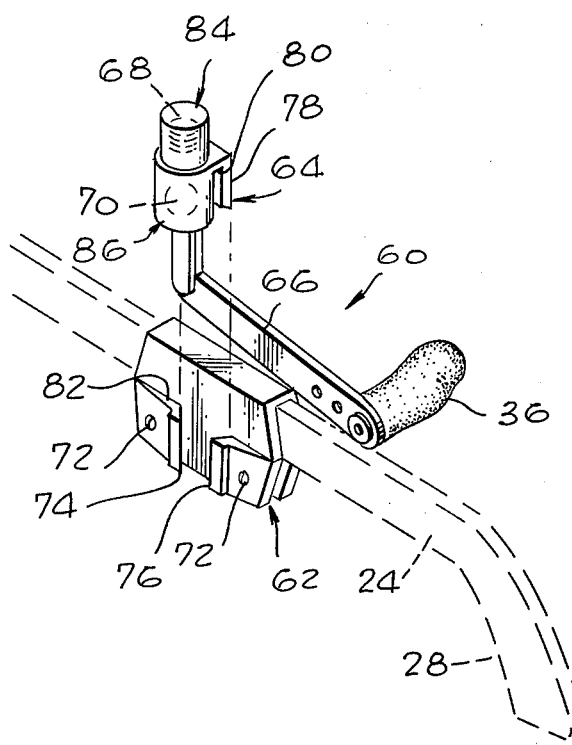
FIG. 5 is an exploded perspective view of an ear protector assembly constructed in accordance with another embodiment of the invention.

FIG. 1 illustrates a pair of ear protector assemblies 10, 12 that are mounted on an eyeglass 14 that includes an eyeglass frame 16 and a pair of shatter resistant lenses 18, 20. The lenses 18, 20 may be of zero corrective power for those workmen or other wearers not otherwise requiring eyeglasses, and may be of a shape that corrects for vision defects for those workmen that require it. The frame includes a front section 22 that mounts on the bridge of the nose and a pair of temple bars 24, 26 hinged to the front section and having a pair of ear loops 28, 30 that loop over the ears. Each ear protector assembly includes a mount 32 that is attached to a temple bar of the eyeglass frame, an earplug holder or arm 34 which is connected to the mount 32, and an earplug 36 that fits into an ear of the wearer. The two ear protector assemblies 10, 12 are identical, but each is assembled with the earplug 36 mounted on the side of its arm 34 which faces the wearer.

As also illustrated in FIGS. 2–4, the mount 32 has three walls, including an inside wall 38 (FIG. 4), an outside wall 40, and a connecting wall 42 at the top. These walls form a slot 43 that receives the temple bar 24 of the eyeglass frame. The mount is of a resilient material such as a typical low cost plastic, and the walls 38, 42 are thin enough to deflect and clamp against the temple bar 24. A pair of screws 44 extending between the two walls 38, 40 can draw the walls together to clamp the mount at any position along the temple bar 24. The inner wall 38 has an inwardly extending wall portion 46 through which the screws 44 extend. The portion 46 can contact the temple of the workman or other wearer to spread the temple bars 24, 26 slightly further apart than normal; this can result in more inward force against the temples of the wearer to stabilize the eyeglasses on the wearer when the earplugs are in his ear.

The mount 32 has a pair of bearing or socket walls 48, 50 that form a recess or socket 52 that is part of a sphere. The arm 34 has a ball 54 at the inner end thereof which is held in the socket 52, to form a universal coupling 55. Accordingly, the arm 34 is universally pivotable on the mount; that is, it can pivot in any direction about the center of the ball 54. The arm 34 has an inner end portion 56 which extends downwardly from the ball 54 through an opening 58 at the bottom of the socket to help stabilize the arm position, and has an outer end portion 60 that extends rearwardly from the bottom of the inner portion 58. The outer portion 60 is of strip-like shape and has three holes 62, 64, 66 extending therethrough. The earplug 36 includes a pod 68 with a tip portion 70 that fits partially into the ear canal of the wearer, and a flat base portion 72 that lies flush against the face of the outer arm portion 60. A screw 74 is embedded in the pod and has a threaded shank that extends through one of the holes 62 in the arm. A nut 76 threaded onto the screw 74 holds the earplug securely to the arm 34.

The ear protector assembly 10 is mounted on the temple bar 24 by slipping the mount 32 through the ear loop 28 or by removing the screws 44, hanging the mount on the straight portion of the temple bar, and reinstalling and partially tightening the screws. The workman then places the eyeglass frame 16 on his head and manipulates the ear protector assembly so that the tip of the earplug 36 can enter his ear canal. Such manipulation includes sliding the mount 32 along the temple bar 24 and pivoting the arm 34. It also may be necessary to install the earplug 36 in a different one of the three holes 62–64 of the arm. After the assembly is in a configuration wherein the earplug properly enters the ear, the workman pivots the arm 34 outwardly to remove the earplug, takes off the eyeglasses, and tightens the screws 44. The position of the mount is then securely fixed along the temple bar, to facilitate subsequent use of the apparatus.

When the workman beings work in an environment which requires eye and ear protection, he merely picks up the eyeglass and ear protector assembly, places it on his head with the ear loops 28, 30 looped over his ears, and then pivots the arms 34 of the ear protector assemblies inwardly. The universal joint 55 formed by the ball 54 and socket 52 permits considerably manipulation by the workman to firmly seat the tip of the earplug in his ear, and yet the workman is assured of bringing the earplug to his ear canal with little effort. The socket walls 48, 50 of the mount can resiliently move apart and together a small distance and the ball 54 is of a size to maintain the walls biased apart. This results in high friction at the universal joint 55, so that the arm 34 tends to retain its position. In spite of the high friction at the joint 55, pivoting of the arm in any direction is easily accomplished by a workman.

It would be possible to construct the mount 32 so that it smoothly slides on the temple bar 24 in everyday use. However, temple bars vary in thickness and height, so that it is difficult to provide a low cost mount that will smoothly slide on any temple bar. Furthermore, it is difficult to control sliding friction to maintain it at a constant level, and in fact, jamming tends to occur in low cost slider bearings where there is moderate friction. This can be contrasted with pivotal mounting wherein a moderate pivotal friction, without jamming, can be maintained with low cost parts. In adjusting the earplug positions, a workman merely has to move the arm 34 about a pivot joint, so that the action is smooth and the earplug is held against his ear after being inserted therein. The inwardly-extending wall portion 46 on each mount, which bears against the temple of the wearer, tends to spring apart the temple bars 24, 26, so that the apparatus presses with a low but definite pressure on the temple. This normally eliminates any slight looseness of the temple bars which is sometimes present in eyeglass frame that the wearer considers as properly fitting him. This slight outward spreading of the temple bars permits the earplugs to press inwardly with a slight force against the ear canal so that the earplugs are firmly seated therein. When the earplugs are fitted into the ear, they prevent forward movement of the eyeglass frame, so the frame does not slip forward onto the bridge of the nose, but is held firmly in place.

Figure 6:
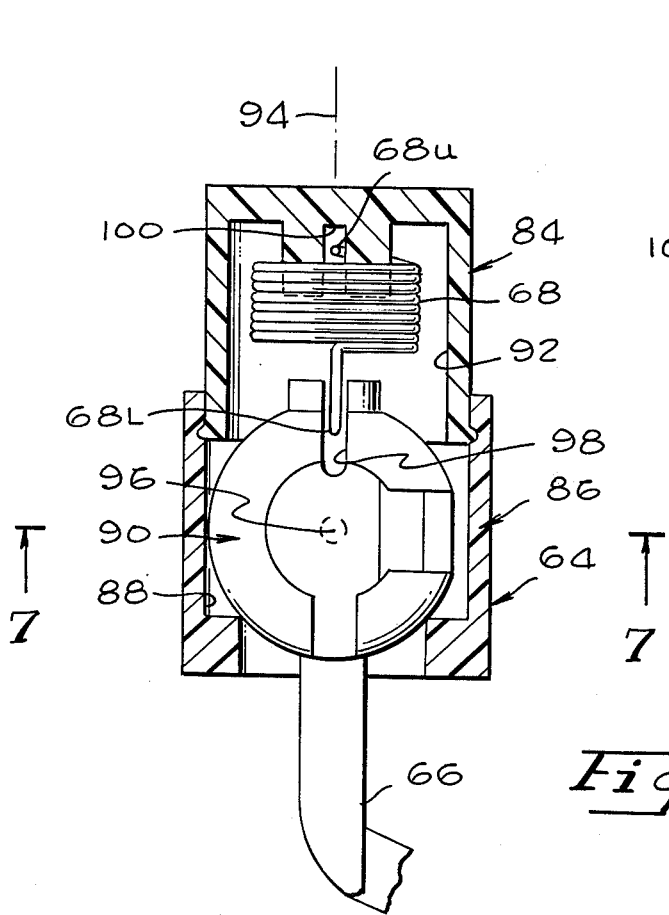
FIG. 6 is a partial sectional side view of the assembly of FIG. 5.
Figure 7:
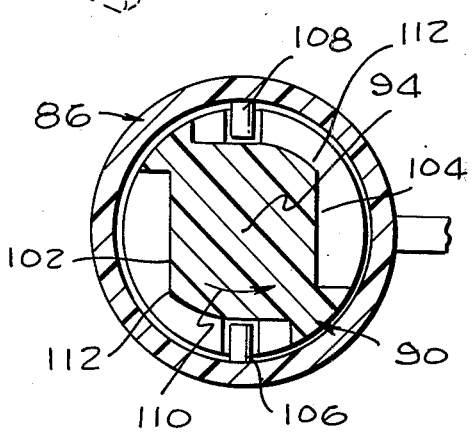
FIG. 7 is a view taken on line 7—7 of FIG. 6.

FIGS. 5–7 illustrate another ear protector assembly 60, which is also designed for installation on the temple bar 24 of an eyeglass, but which has even greater versatility. The assembly 60 includes a first mount member 62 supported on the temple bar at a location forward of the temple bar portion 28 that is received behind the ear. A second mount member 64, which pivotally supports an elongated holder 66 having a rearward end on which the earplug 36 is mounted, is designed to be rapidly attached and detached from the first mount member 62. The assembly also includes a spring 68 which urges the holder to pivot towards the ear to hold the earplug firmly in place, and a brake 70 which can hold the earplug away from the ear in spite of the spring. A corresponding assembly is provided for the other temple bar of the eyeglass.

The first mount member 62 is of a construction similar to the mounts 32, 34 of FIG. 1, and includes a pair of screws 72 for fixing the mount position along the temple bars. However, the mount member 62 also includes a pair of receiving rails 74, 76 for detachably receiving the second mount member, by sliding down a dovetail slide 78 of the second mount member until a ledge 80 on the second mount member abuts a ledge 82 on the first mount member. The rails can be formed by any two wall portions that are not part of a circle, since the function of the rails is to permit slideable reception and prevent rotation after such reception. A workman installs the ear protector assembly by adjusting it to properly fit his ear, and then tightening the screws 72 to fix the position of the first mount member. Thereafter, the workman can remove the second mount member 64, with the holder and earplug thereon, from the first mount member at the end of each work day. This enables the workman to wear the eyeglass after working hours without the earplugs or other highly noticeable attachments thereon. Only the first mount members 62 remain on the eyeglass frame, and they are normally not easily noticeable. At the beginning of the next working day, the workman merely slips the second mount member 64 onto the first one 62. The second mount member 64 is always returned to the same position, wherein the ledges 80 and 82 abut, and therefore the earplugs will always be positioned for rapid pivoting against the ear.

The second mount member 64 includes upper and lower parts 84, 86 (FIG. 6) that form a socket 88 that holds a ball 90 at one end of the earplug holder 66 and that form a chamber 92 that holds the torsion spring 68. The ball 90 can pivot about a vertical axis 94 to move the earplug towards and away from the ear, and can also pivot about a horizontal axis 96 to raise or lower the earplug. The torsion spring 68 is designed to urge the earplug towards the ear so that it presses with a force of several ounces against the ear to keep out noise, and yet to produce little if any upward or downward bias that would create unnecessary added force on the ear and that might tend to dislodge the earplug from its proper position at the entrance to the ear canal. This is accomplished by forming a slot 98 at the top of the ball 90 and by positioning the lower end 68L of the spring loosely in the slot. The upper end 68U of the spring is loosely installed in a slot 100 of the second mount member 64.

The spring 68 is installed with a torsional preload (as by rotating the upper mount part 84 by part of a turn before fixing it to the lower part 86), so that the ball is urged to pivot about the vertical axis 94 to thereby urge the earplug into the ear. However, a limited degree of pivoting of the ball about any horizontal axis such as 96 can be performed without appreciable resistance from the spring. Thus, no appreciable upward or downward bias is imparted for a range of heights of the earplug, and yet a strong inward bias is produced, all in a simple and economical mechanism.

There are many applications where a workman wants to repeatedly move the earplugs 36 away from his ears for a short time and then back against his ears, as where the high intensity noise is intermittent. The ear protector assembly 60 permits this to be easily accomplished by providing a brake 70 that can hold the earplug away from the ear in spite of the biasing of the spring 68. As best shown in FIG. 7, the ball 90 includes a pair of non-circular slots 102, 104; that is, the slots are not at a constant radius from the vertical pivot axis 94. A pair of brake portions in the form of pins 106, 108 fixed to the lower part 86 of the second mount member, lie in the grooves 102, 104 near the bottoms of the grooves. When the ball 90 is pivoted far in the direction of arrow 110, to move the earplugs away from the ear, the pins ride over corner portions 112 of the slots where the bottoms of the slots are furthest from the pivot axis 94. A workman can easily apply enough torque to pivot the ball so that the pins pass the corners, but the spring 68 cannot apply sufficient torque to move the ball back across the corners. Accordingly, the earplugs remain away from the ears until a workman pivots the holder 66 back towards the ears so the pins again pass the camming surfaces or corners 112. Thereafter, the ball pivots easily, and the spring can hold the earplugs against the ear.

Thus, the invention provides a low cost ear protector assembly which is used in conjunction with eyeglasses so that a workman has to store and handle only one item to protect his eyes and ears, and with the bulk of the combination being only slightly greater than that of an eyeglass alone. The ear protector assembly includes a mount that can slide along the temple bar and an arm pivotally connected to the mount and carrying an earplug. The mount includes fasteners for fixing its position along the temple bar. Accordingly, a workman merely has to operate the pivot in normal use to remove and replace the earplug, the use of only pivoting for this operation resulting in smooth operation with low cost parts. While it would be possible to utilize an arm that pivots about a single axis, the use of a universal pivot makes the mount very simple and still permits rapid installation of the earplug in everyday use. In one embodiment of the invention, the mount has two members, one always fixed on the eyeglass and the other being easily detached and reattached and carrying the earplug holder and earplug. A spring urges the holder to pivot towards the ear but without interfering with up and down pivoting, and a brake can hold the earplug away from the ear.

Although particular embodiments of the invention has been described and illustrated herein, it is recognized that modifications and variations may readily occur to those skilled in the art and consequently it is intended that the claims be interpreted to cover such modifications and equivalents.

The embodiments of the invention in which an exclusive property or privilege is claimed are defined as follows:

1. An ear protector for mounting on an eyeglass frame that has temple bars, comprising:
   a mount having means for mounting on the temple bar of an eyeglass frame in front of the temple bar portion that lies on the ear;
   an earplug holder having a first end formed to mount on said mount and a second end;
   an earplug mounted on the second end of the earplug holder;
   a universal pivot which couples said mount to said first end of said holder, to permit the holder to pivot about a first axis, so that the earplug can be moved up and down, and to permit the holder to pivot about a second axis which is angled from said first axis, so that the earplug can be also moved toward and away from the head; and
   spring means coupled to said earplug holder for urging the holder to pivot in a predetermined direction about said second axis with substantially no bias about said second axis, whereby the earplug is urged towards the head with substantially no up or down bias.

2. The ear protector described in claim 1 including:
   brake means coupled to said holder and operable only at a predetermined pivotal position of said holder about said second axis, wherein the earplug lies away from the head, for retaining said holder against pivoting in a predetermined direction about said second axis, whereby to retain said holder against pivoting toward the head under the force of said spring.

3. An ear protector for mounting on an eyeglass frame that has temple bars, comprising:
   a first mount member having a slot for slideably receiving a temple bar, said mount member having fastener means for clamping the first mount member along the temple bar that lies in said slot, and said mount member having walls forming first rail means for receiving another rail means;
   a second mount member having second rail means removably attached to the first rail means on the first mount member for permitting rapid attachment of said second mount member at a predetermined location and orientation thereon and rapid removal therefrom;
   an elongated earplug holder having a first end mounted on said second mount member and a second end; and
   an earplug mounted on the second end of said earplug holder, whereby to enable a workman to easily remove the earplug from the eyeglass frame and then replace it at a prefixed position that assures that the earplugs will lie opposite his ear.

4. An ear protector for mounting on apparatus which is worn on the head, comprising:
   a mount having a tubular portion with an open end;
   an earplug and holder assembly including a lever member with an earplug at one end and a ball at the other end, said ball lying in said tubular portion of said mount and said ball having a slot; and a torsion spring disposed in said tubular portion and having a first spring end coupled to the mount and a second spring end loosely received in said slot in said ball, whereby to urge the holder assembly to pivot in one direction so it can press against the ear and yet to permit the holder assembly to easily pivot in other directions to lie at the proper height to reach the ear.

5. The ear protector described in claim 4 wherein: said ball and said mount having brake portions that engage one another as said ball is pivoted in a direction against the spring bias to a predetermined position, said brake portions including means for holding the ball against pivoting back under the force of said spring when the brake portions are engaged, whereby to enable a workman to leave the earplugs away from his ears.

6. Apparatus for protecting the eyes and ears comprising:

an eyeglass having a frame with a pair of lens openings and a pair of temple bars (24), the eyeglass also including a pair of lenses mounted in said lens openings;

a first mount member (62) having walls forming a slot which is wider than a portion of one of said temple bars for receiving one of said temple bars, said first mount member having fastener means (72) for clamping the walls of the slot onto a temple bar which lies in said slot to fix the position of the mount member thereon, and said mount member having a pair of rails (74, 76);

a second mount member (64) slideable onto and off from said rails to permit rapid attachment and detachment from said first mount member, said second member forming a ball-receiving socket (88) and a spring holding chamber (92);

an earplug holder (66) having a ball (90) at one end and an earplug (36) at the other end, said ball being disposed in said socket, and said ball having a slot (98) therein;

a torsion spring (68) lying in said chamber, with one end (68U) of the spring coupled to said second mount member and the other end (68L) loosely received in said slot (98) of said ball, whereby the spring urges the holder to pivot about a substantially vertical axis (94) to urge the earplug into the ear while not producing a substantial bias throughout limited pivoting about a horizontal axis (96) to raise and lower the earplug;

said ball having a camming surface (112), and said second mount member having a brake portion (106) including means for engaging said camming surface (112) when the holder is pivoted away from the ear, to resist return pivoting of the holder under the force of said torsion spring.

7. Apparatus for protecting the eyes and ears, comprising:

an eyeglass having a frame with a pair of lens openings and a pair of temple bars, the eyeglass also including a pair of lenses mounted in said lens openings, said temple bars extending substantially normal to said lenses;

a pair of mounts, each having means securely engaging and mounting one of said mounts on a different one of said temple bars at a location spaced forward from the rear end of the temple bar to lie forward of the ear when the rear end of the temple bar lies behind the ear;

a pair of earplug holders, each having a forward end pivotally mounted on a corresponding one of said mounts and a rearward end which can be positioned to lie rearward of the forward end so as to lie opposite the middle of the ear; and a pair of earplugs, each mounted on the rearward end of a corresponding earplug holder;

each of said mounts forming a socket and each of said holders having a ball at the forward end thereof which is held in the socket of the corresponding mount, to permit the holder to pivot about a first axis to move the earplug up and down as well as about a second axis to move the earplug towards and away from each other to thereby move toward and away from the ear of the wearer; and including a pair of torsion spring means, each coupling a mount to a ball and loosely held to at least one of them, said spring means biasing each earplug holder towards the other to pivot about said second axis so the earplug moves against the ear, while providing substantially no bias to pivoting about said first axis.

8. Apparatus for protecting the eyes and ears, comprising:

an eyeglass having a frame with a pair of lens openings and a pair of temple bars, the eyeglass also including a pair of lenses mounted in said lens openings, said temple bars extending substantially normal to said lenses;

a pair of mounts, each having means securely engaging and mounting one of said mounts on a different one of said temple bars at a location spaced forward from the rear end of the temple bar to lie forward of the ear when the rear end of the temple bar lies behind the ear;

a pair of earplug holders, each having a forward end pivotally mounted on a corresponding one of said mounts and a rearward end which can be positioned to lie rearward of the forward end so as to lie opposite the middle of the ear;

a pair of earplugs, each mounted on the rearward end of a corresponding earplug holder;

a pair of spring means, each coupled to the forward end of an earplug holder and biasing the holder to pivot inwardly towards the other holder and therefore towards the head of the wearer; and a pair of brake means coupled to the forward ends of said earplug holders for preventing pivoting of the holders towards one another under the biasing of a corresponding spring when the holders are pivoted to a predetermined outward portion away from each other, whereby to hold the earplugs away from the wearer.

9. Ear protection apparatus for use on an eyeglass having a frame with a pair of lens openings containing lenses and a pair of temple bars, comprising:

a pair of mounts having slot means receiving the temple bars of an eyeglass, whereby the mounts can be located at a range of positions along the temple bars;

a pair of earplug holders, each having a forward end pivotally mounted on a corresponding one of said mounts and a rearward end; and a pair of earplugs, each mounted on the rearward end of a corresponding earplug holder;

each mount including a socket and each earplug holder including a ball at its forward end which is received in said socket, whereby to permit the holder to be pivoted up and down so it can lie opposite the ear canal, as well as toward and away from the ear to move against and away from the ear canal.

10. Ear protection apparatus for use on an eyeglass having a frame with a pair of lens openings containing lenses and a pair of temple bars, comprising:
- a pair of mounts having means for attachment at a plurality of fixed positions on the temple bars of an eyeglass;
- a pair of earplug holders, each having a forward end pivotally mounted on a corresponding one of said mounts and a rearward end; and
- a pair of earplugs, each mounted on the rearward end of a corresponding earplug holder;
- each of said mounts has a first member which includes said means for attachment on a temple bar and a second member carrying the forward end of one of said holders on which one of said earplugs is mounted, said second member including means for rapid attachment and detachment from said first member, whereby a worker can wear his eyeglasses after working hours with only the first mount member thereon so that when he begins work again he can rapidly attach the first member with the holder and earplug thereon.

* * * * *